(12) United States Patent
Subramanyam et al.

(10) Patent No.: US 10,251,823 B2
(45) Date of Patent: Apr. 9, 2019

(54) ORAL CARE COMPOSITION CONTAINING ZINC SALTS AND CALCIUM CARBONATE

(71) Applicant: Colgate-Palmolive Company, New York, NY (US)

(72) Inventors: Ravi Subramanyam, Belle Mead, NJ (US); Suzanne Jogun, Wayne, NJ (US); Mahmoud Hassan, Somerset, NJ (US); Navin Lewis, Mumbai (IN); Xiao Yi Huang, Guangzhou (CN); Shao Peng Xu, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/525,381

(22) PCT Filed: Nov. 13, 2015

(86) PCT No.: PCT/US2015/060563
§ 371 (c)(1),
(2) Date: May 9, 2017

(87) PCT Pub. No.: WO2016/077688
PCT Pub. Date: May 19, 2016

(65) Prior Publication Data
US 2017/0333310 A1 Nov. 23, 2017

(30) Foreign Application Priority Data
Nov. 14, 2014 (IN) .............. 3300/DEL/2014

(51) Int. Cl.
| | |
|---|---|
| *A61K 8/27* | (2006.01) |
| *A61K 8/25* | (2006.01) |
| *A61K 8/365* | (2006.01) |
| *A61Q 11/00* | (2006.01) |
| *A61K 8/02* | (2006.01) |
| *A61K 8/04* | (2006.01) |
| *A61K 8/19* | (2006.01) |
| *A61K 8/21* | (2006.01) |
| *A61K 8/37* | (2006.01) |

(52) U.S. Cl.
CPC .............. *A61K 8/27* (2013.01); *A61K 8/0237* (2013.01); *A61K 8/042* (2013.01); *A61K 8/19* (2013.01); *A61K 8/21* (2013.01); *A61K 8/25* (2013.01); *A61K 8/365* (2013.01); *A61K 8/37* (2013.01); *A61Q 11/00* (2013.01)

(58) Field of Classification Search
CPC ........................................................ A61K 8/27
See application file for complete search history.

(56) References Cited

U.S. PATENT DOCUMENTS

| | | | |
|---|---|---|---|
| 2012/0034280 A1* | 2/2012 | Cohen ...................... | A61K 8/20 424/401 |
| 2015/0328094 A1 | 11/2015 | Xu et al. | |
| 2016/0000667 A1 | 1/2016 | Potnis et al. | |

FOREIGN PATENT DOCUMENTS

| | | |
|---|---|---|
| WO | WO 2006/050777 | 5/2006 |
| WO | WO 2014/100928 | 7/2014 |
| WO | WO 2014/147630 | 9/2014 |

OTHER PUBLICATIONS

International Search Report and Written Opinion in International Application No. PCT/US2015/060563, dated May 31, 2016.

\* cited by examiner

*Primary Examiner* — Benjamin J Packard

(57) ABSTRACT

The present invention provides an oral care composition comprising: (a) a first composition comprising a silica abrasive and a first zinc compound selected from zinc citrate, zinc chloride, zinc acetate, zinc lactate, zinc salicylate, zinc sulfate, and zinc nitrate; and (b) a second composition comprising a calcium carbonate abrasive; wherein the first composition and/or the second composition further comprises a second zinc compound selected from zinc oxide, zinc carbonate and zinc tartrate; and wherein the oral care composition optionally further comprises from 0.1 to 1.75 weight % of a tartar control agent, based on the total weight of the oral care composition.

19 Claims, No Drawings

ORAL CARE COMPOSITION CONTAINING ZINC SALTS AND CALCIUM CARBONATE

BACKGROUND

Dental plaque is a biofilm that adheres to tooth and other oral surfaces, particularly at the gingival margin, and is implicated in the occurrence of gingivitis, periodontitis, caries and other forms of periodontal disease. Various antibacterial agents can retard the growth of bacteria and thus reduce the formation of biofilm on oral surfaces. Zinc salts have been previously used as antibacterial agents. Without being bound by any theory, free zinc ions are believed to provide antibacterial efficacy by inhibition of glucose metabolism and/or interaction with the bacterial cell wall, reducing bacterial colonization of the oral cavity (as discussed in Cummins D., *J. Clin. Periodontol.* 1991; 18; 455-461). An insoluble zinc compound, zinc oxide, could also deliver strong antibacterial efficacy during tooth brushing. However, soluble zinc salts, such as zinc citrate, may react with calcium carbonate to form insoluble zinc carbonate, thus reducing the amount of zinc ions available for delivery to the tooth surface. Some consumers, however, prefer dentifrice compositions comprising a calcium carbonate abrasive (rather than a silica abrasive) due to their high cleaning efficacy. Calcium carbonate abrasives may also provide a cost advantage as compared to other types of abrasive.

It would therefore be desirable to provide an oral care composition which comprises a calcium carbonate abrasive, but which also maintains the high antibacterial and biofilm reduction efficacy of zinc salts present in the composition.

BRIEF SUMMARY

In a first aspect, the present invention provides an oral care composition comprising: (a) a first composition comprising a silica abrasive and a first zinc compound selected from zinc citrate, zinc chloride, zinc acetate, zinc lactate, zinc salicylate, zinc sulfate, and zinc nitrate; and (b) a second composition comprising a calcium carbonate abrasive and a second zinc compound selected from zinc oxide, zinc carbonate and zinc tartrate; wherein the oral care composition further comprises from 0.1 to 1.75 weight % of a tartar control agent, based on the total weight of the oral care composition.

Optionally, the concentration of the first zinc compound in the oral care composition is from 0.25 to 0.75 weight %, based on the total weight of the oral care composition. Further optionally, the concentration of the first zinc compound in the oral care composition is from 0.4 to 0.6 weight %, based on the total weight of the oral care composition.

Optionally, the concentration of the second zinc compound in the oral care composition is from 0.5 to 1.5 weight %, based on the total weight of the oral care composition. Further optionally, the concentration of the second zinc compound in the oral care composition is from 0.8 to 1.2 weight %, based on the total weight of the oral care composition.

Optionally, the weight ratio of the second zinc compound to the first zinc compound in the oral care composition is from 1.5:1 to 4.5:1. Further optionally, the weight ratio of the second zinc compound to the first zinc compound in the oral care composition is from 1.5:1 to 3:1, optionally about 2:1.

Optionally, the first zinc compound is zinc citrate.
Optionally, the second zinc compound is zinc oxide.

Optionally, the concentration of the silica abrasive in the oral care composition is from 1 to 10 weight %, based on the total weight of the composition. Optionally, the concentration of the silica abrasive in the first composition is from 5 to 20 weight %, based on the weight of the first composition.

Optionally, the concentration of the calcium carbonate abrasive in the oral care composition is from 20 to 40 weight %, based on the total weight of the composition. Optionally, the concentration of the calcium carbonate abrasive in the second composition is from 35 to 50 weight %, based on the weight of the second composition.

Optionally, the first composition is a toothpaste. Alternatively, the first composition is a gel.

Optionally, the second composition is a toothpaste.

Optionally, the weight ratio of the first composition to the second composition is from 1:8 to 1:1. Further optionally, the weight ratio of the first composition to the second composition is from 1:5 to 1:3, optionally about 1:4.

Optionally, the oral care composition is a striped dentifrice comprising a main dentifrice material and a stripe dentifrice material, the first composition being the stripe dentifrice material and the second composition being the main dentifrice material.

Optionally, the tartar control agent is a monobasic, dibasic or tribasic sodium phosphate; a mono-, di- or trisodium pyrophosphate; a mono-, di- or tripotassium pyrophosphate: tetrasodium pyrophosphate (TSPP); tetrapotassium pyrophosphate (TKPP); sodium or potassium tripolyphosphate; sodium or potassium tetrapolyphosphate; sodium or potassium trimetaphosphate; sodium or potassium hexametaphosphate; or a combination of any two or more thereof. Further optionally, the tartar control agent is tetrasodium pyrophosphate, tetrapotassium pyrophosphate, or a combination thereof.

Optionally, the total concentration of the tartar control agent in the oral care composition is from 0.2 to 1.5 weight %, based on the total weight of the oral care composition. Further optionally, the total concentration of the tartar control agent in the oral care composition is from 0.25 to 1.0 weight %, based on the total weight of the oral care composition. Still further optionally, the total concentration of the tartar control agent in the oral care composition is from 0.25 to 0.75 weight %, based on the total weight of the oral care composition. Yet further optionally, the total concentration of the tartar control agent in the oral care composition is from 0.4 to 0.6 weight %, based on the total weight of the oral care composition.

Optionally, the tartar control agent is present in both the first composition and the second composition and the weight ratio of tartar control agent present in the first composition to tartar control agent present in the second composition is from 1:5 to 1:3, optionally about 1:4. Alternatively, the tartar control agent is present in the first composition, and the second composition is free of tartar control agent.

In a second aspect, the present invention provides an oral care composition of the present invention, for use in reducing or inhibiting biofilm formation in an oral cavity.

In a third aspect, the present invention provides a method of reducing or inhibiting biofilm formation in an oral cavity, the method comprising contacting the oral cavity with an oral care composition of the present invention.

In a fourth aspect, the present invention provides a method of enhancing the biofilm reduction efficacy of an oral care composition comprising a calcium carbonate abrasive and at least one zinc salt, the method comprising providing the oral care composition as an oral care composition of the present invention.

In a fifth aspect, the present invention provides a method of enhancing the antibacterial efficacy of an oral care composition comprising a calcium carbonate abrasive and at least one zinc salt, the method comprising providing the oral care composition as an oral care composition of the present invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight based on the total weight of the oral care composition. The amounts given are based on the active weight of the material. In addition, all ratios expressed herein refer to ratios by weight unless otherwise indicated.

Unless otherwise specified, all experiments described herein are conducted at 25° C. and under atmospheric pressure.

As discussed above, it would be desirable to provide an oral care composition which comprises a calcium carbonate abrasive, but which also maintains the high antibacterial and biofilm reduction efficacy of zinc salts present in the composition.

Therefore, in one aspect of the present invention, there is provided an oral care composition comprising: (a) a first composition comprising a silica abrasive and a first zinc compound selected from zinc citrate, zinc chloride, zinc acetate, zinc lactate, zinc salicylate, zinc sulfate, and zinc nitrate; and (b) a second composition comprising a calcium carbonate abrasive and a second zinc compound selected from zinc oxide, zinc carbonate and zinc tartrate; wherein the oral care composition further comprises from 0.1 to 1.75 weight % of a tartar control agent, based on the total weight of the oral care composition.

The present inventors have surprisingly found that such an oral care composition provides enhanced biofilm reduction efficacy as compared to compositions where the zinc salts are simply incorporated into a calcium carbonate-based dentifrice. The present inventors have also surprisingly found that the oral care compositions of the present invention provide enhanced biofilm reduction efficacy as compared to equivalent oral care compositions wherein the second zinc compound is instead included in the silica abrasive-based composition and the first zinc compound is included in the calcium carbonate-based composition.

In addition, the present inventors have also surprisingly found that the oral care compositions of the present invention provide enhanced biofilm reduction efficacy as compared to equivalent oral care compositions which contain a higher concentration of tartar control agent.

In some embodiments, the concentration of first zinc compound in the oral care composition is from 0.1 to 1 weight %, from 0.2 to 0.8 weight %, from 0.25 to 0.75 weight %, from 0.3 to 0.7 weight %, from 0.4 to 0.6 weight %, or about 0.5 weight %, based on the total weight of the oral care composition.

In some embodiments, the concentration of the second zinc compound in the oral care composition is from 0.2 to 2 weight %, from 0.25 to 1.75 weight %, from 0.4 to 1.6 weight %, from 0.5 to 1.5 weight %, from 0.7 to 1.4 weight %, from 0.75 to 1.3 weight %, from 0.8 to 1.2 weight %, from 0.9 to 1.1 weight %, or about 1 weight %, based on the total weight of the oral care composition.

In certain embodiments, the concentration of the second zinc compound in the oral care composition is from 0.2 to 2 weight % and the concentration of the first zinc compound in the oral care composition is from 0.1 to 1 weight %, based on the total weight of the oral care composition. In certain embodiments, the concentration of the second zinc compound in the oral care composition is from 0.4 to 1.6 weight % and the concentration of the first zinc compound in the oral care composition is from 0.2 to 0.8 weight % based on the total weight of the oral care composition. In certain embodiments, the concentration of the second zinc compound in the oral care composition is from 0.7 to 1.4 weight % and the concentration of the first zinc compound in the oral care composition is from 0.3 to 0.7 weight %, based on the total weight of the oral care composition. In certain embodiments, the concentration of the second zinc compound in the oral care composition is about 1 weight % and the concentration of the first zinc compound in the oral care composition is about 0.5 weight %, based on the total weight of the oral care composition.

In some embodiments, the weight ratio of the second zinc compound to the first zinc compound in the oral care composition is from 1.5:1 to 4.5:1; from 1.5:1 to 4:1; from 1.5:1 to 3:1; from 1.7:1 to 2.3:1; from 1.9:1 to 2.1:1; or about 2:1.

In some embodiments, the first composition is free of the second zinc compound and the second composition is free of the first zinc compound. By the first composition being "free of the second zinc compound", it is meant that the concentration of the second zinc compound in the first composition is less than 0.05 weight %, based on the weight of the first composition. By the second composition being "free of the first zinc compound", it is meant that the concentration of the first zinc compound in the second composition is less than 0.01 weight %, based on the weight of the second composition.

In any of the above-described embodiments, the first zinc compound may be zinc citrate (ZnCit). The zinc citrate may be present as zinc citrate trihydrate.

In any of the above-described embodiments, the second zinc compound may be zinc oxide (ZnO).

In some embodiments, the concentration of the silica abrasive in the oral care composition is from 0.5 to 15 weight %, from 1 to 10 weight %, from 1.5 to 8 weight %, from 2 to 5 weight %, or from 3 to 4 weight %, based on the total weight of the composition. In certain embodiments, the concentration of the silica abrasive in the first composition is from 5 to 20 weight %, from 8 to 18 weight %, from 12 to 17 weight %, or from 14 to 16 weight %, based on the weight of the first composition. Suitable silica abrasives include, but are not limited to, precipitated or hydrated silicas (such as Zeodent 105 and Zeodent 114 marketed by J. M. Huber Chemicals Division, Havre de Grace, Md. 21078); Sylodent 783 (marketed by Davison Chemical Division of W. R. Grace & Company); or Sorbosil AC 43 (from PQ Corporation).

In some embodiments, the concentration of the calcium carbonate abrasive in the oral care composition is from 20 to 40 weight %, from 25 to 38 weight %, from 30 to 35 weight %, or from 32 to 34 weight %, based on the total weight of the composition. In certain embodiments, the concentration of the calcium carbonate abrasive in the second composition is from 35 to 50 weight %, from 37 to 48 weight %, from 39 to 45 weight %, or from 41 to 43 weight %, based on the weight of the second composition. Suitable calcium carbonate abrasives include precipitated calcium carbonate (PCC) and natural calcium carbonate (NCC). In some embodiments, the calcium carbonate abrasive is NCC.

In some embodiments, the first composition is free of calcium carbonate abrasives, and the second composition is free of silica abrasives. By the first composition being "free of calcium carbonate abrasives", it is meant that the amount of calcium carbonate abrasive in the first composition is less than 0.05 weight %, based on the weight of the first composition. By the second composition being "free of silica abrasives", it is meant that the concentration of silica abrasives in the second composition is less than 0.05 weight %, based on the weight of the second composition.

In some embodiments, the first composition is a toothpaste. In other embodiments, the first composition is a gel. In some embodiments, the second composition is a toothpaste.

In some embodiments, both the first and second compositions are toothpastes. In other embodiments, the first composition is a gel and the second composition is a toothpaste.

In some embodiments, the weight ratio of the first composition to the second composition is from 1:8 to 1:1; from 1:7 to 1:2; from 1:6 to 1:2; from 1:5 to 1:3, or about 1:4.

In some embodiments, the oral care composition is a striped dentifrice comprising a main dentifrice material and a stripe dentifrice material, the first composition being the stripe dentifrice material and the second composition being the main dentifrice material. In other such embodiments, the second composition is the stripe dentifrice material and the first composition is the main dentifrice material.

Suitable tartar control agents (otherwise known as anti-calculus agents) include, but are not limited to: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids, and salts of any of these agents (for example, their alkali metal and ammonium salts). In some embodiments, the tartar control agent is a monobasic, dibasic or tribasic sodium phosphate; a mono-, di- or trisodium pyrophosphate; a mono-, di- or tripotassium pyrophosphate; tetrasodium pyrophosphate (TSPP); tetrapotassium pyrophosphate (TKPP); sodium or potassium tripolyphosphate; sodium or potassium tetrapolyphosphate; sodium or potassium trimetaphosphate; sodium or potassium hexametaphosphate; or a combination of any two or more thereof. In such tartar control agents, sodium or potassium can optionally be replaced by ammonium. In some embodiments, the tartar control agent is tetrasodium pyrophosphate, tetrapotassium pyrophosphate, or a combination thereof.

In addition to controlling tartar, certain tartar controlling agents (such as, for example, pyrophosphates) can also act to stabilize any fluoride present in the compositions, and to mask the taste of zinc.

In some embodiments, the total concentration of the tartar control agent in the oral care composition is from 0.2 to 1.5 weight %; from 0.25 to 1.0 weight %; from 0.25 to 0.75 weight %; from 0.4 to 0.6 weight %; or about 0.5 weight %, based on the total weight of the oral care composition.

In some embodiments, the tartar control agent is present in both the first composition and the second composition and the weight ratio of tartar control agent present in the first composition to tartar control agent present in the second composition is from 1:8 to 1:1; from 1:7 to 1:2; from 1:6 to 1:2; from 1:5 to 1:3, or about 1:4.

In other embodiments, the tartar control agent is present in the first composition, and the second composition is free of tartar control agent. By the second composition being "free of tartar control agent", it is meant that the concentration of tartar control agent in the second composition is less than 0.05 weight %, based on the weight of the second composition. The present inventors have also surprisingly found that inclusion of the tartar control agent solely in the first composition provides the oral care composition with enhanced biofilm reduction efficacy as compared to an equivalent oral care composition in which the tartar control agent is included in both the first and second compositions.

In a second aspect of the present invention, there is provided an oral care composition as described in any of the above embodiments, for use in reducing or inhibiting biofilm formation in an oral cavity.

In a third aspect, the present invention provides a method of reducing or inhibiting biofilm formation in an oral cavity, the method comprising contacting the oral cavity with an oral care composition as described in any of the above embodiments.

In a fourth aspect, the present invention provides a method of enhancing the biofilm reduction efficacy of an oral care composition comprising a calcium carbonate abrasive and at least one zinc salt, the method comprising providing the oral care composition as an oral care composition as described in any of the above embodiments.

In a fifth aspect, the present invention provides a method of enhancing the antibacterial efficacy of an oral care composition comprising a calcium carbonate abrasive and at least one zinc salt, the method comprising providing the oral care composition as an oral care composition as described in any of the above embodiments.

In any embodiments of each of the above aspects, the oral care compositions may further comprise additional ingredients. These additional ingredients may include, but are not limited to, diluents (e.g. water), bicarbonate salts, surfactants, foam modulators, sweeteners, flavorants, pigments, antibacterial agents, anticaries agents, humectants (such as sorbitol or glycerin), preservatives, thickeners (such as thickening silicas), gums (such as xanthan gum or carboxymethylcellulose (CMC)) and mixtures thereof.

In some embodiments, the oral care composition of the invention may also contain a source of fluoride ions or a fluorine-providing ingredient in amounts sufficient to supply 25 ppm to 5,000 ppm of fluoride ions, generally at least 500 ppm, e.g., 500 to 2000 ppm, e.g., 1000-1600 ppm, e.g., 1450 ppm. Fluoride ion sources may be added to the compositions of the invention at a level of 0.01 weight % to 10 weight %, 0.03 weight % to 5 weight %, preferably 0.1 weight % to 1 weight %, most preferably 0.5 to 0.9 weight % of the composition. However, it is to be understood that the weights of fluoride salts to provide the appropriate level of fluoride ion will obviously vary based on the weight of the counter ion in the salt, and one of skill in the art may readily determine such amounts. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source preferably includes stannous fluoride, sodium fluoride, amine fluorides, sodium monofluorophosphate, as well as mixtures thereof.

In some embodiments, the oral care compositions of the present invention comprise at least one bicarbonate salt useful for example to impart a "clean feel" to teeth and gums due to effervescence and release of carbon dioxide. The one or more additional bicarbonate salts are optionally present in a total amount of about 0.1 wt. % to about 20 wt. %, for example about 0.5 wt. % to 10 wt. %, by total weight of the oral care composition.

The oral care compositions of the invention may also comprise at least one surfactant. Any orally acceptable surfactant, most of which are anionic (e.g. sodium lauryl sulfate—SLS), nonionic or amphoteric (e.g. betaine), can be used. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the oral care composition.

The oral care compositions of the invention may comprise at least one foam modulator, useful for example to increase amount, thickness or stability of foam generated by the composition upon agitation. One or more foam modulators are optionally present in a total amount of about 0.1 wt. % to about 10 wt. %, for example from about 0.2 wt. % to about 5 wt. %, or from about 0.25 wt. % to about 2 wt. %, by total weight of the oral care composition.

The oral care compositions of the present invention may comprise at least one sweetener (such as, for example, sodium saccharin), useful for example to enhance taste of the composition. One or more sweeteners are optionally present in a total amount depending strongly on the particular sweetener(s) selected, but typically 0.005 wt. % to 5 wt. %, by total weight of the composition, optionally 0.01 wt. % to 1 wt. %, further optionally 0.1 wt. % to 0.5 wt. % by total weight of the oral care composition.

The oral care compositions of the present invention may also comprise at least one flavorant, useful for example to enhance taste of the composition. One or more flavorants are optionally present in a total amount of from about 0.01 wt. % to about 5 wt. %, for example, from about 0.03 wt. % to about 2.5 wt. %, optionally about 0.05 wt. % to about 1.5 wt. %, further optionally about 0.1 wt. % to about 0.3 wt. % by total weight of the oral care composition. The first and second compositions may contain different flavorants.

The oral care compositions of the invention may comprise at least one colorant. Colorants herein include pigments, dyes, lakes and agents imparting a particular luster or reflectivity such as pearling agents. Any orally acceptable colorant can be used. One or more colorants are optionally present in a total amount of from about 0.0001 wt. % to about 5 wt. %, for example, from about 0.0001 wt. % to about 1 wt. %, or from about 0.0005 wt. % to about 0.1 wt. %, by total weight of the oral care composition. The first and second compositions may contain different colorants.

The oral care compositions may also comprise a fluoride ion source such as, for example, a monofluorophosphate (MFP). Fluoride ion sources may be added to the oral care compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts.

The oral care compositions of the present invention may comprise a saliva stimulating agent useful, for example, in amelioration of dry mouth. One or more saliva stimulating agents are optionally present in saliva stimulating effective total amount.

The oral care compositions of the present invention may include antisensitivity agents. Such agents may be added in effective amounts, e.g., from about 1 wt. % to about 20 wt. % by weight based on the total weight of the oral care composition, depending on the agent chosen.

The oral care composition of the invention may further comprise an antioxidant.

EXAMPLES

Example 1

Eight dentifrice compositions (Compositions 1 to 8) were formulated.

Compositions 1 to 6 each contained 0.5 weight % zinc citrate (ZnCit) and 1 weight % zinc oxide (ZnO), based on the total weight of the composition (which, for the striped compositions, is the combined weight of the calcium carbonate-based main dentifrice component and the silica abrasive-based stripe component).

Composition 1 was a silica abrasive-based non-striped toothpaste, which also contained 0.5 weight % tetrasodium pyrophosphate (TSPP).

Composition 2 was a striped toothpaste with a calcium carbonate-based main dentifrice component and a silica abrasive-based stripe component. The weight ratio of the main dentifrice component to the stripe component was 80:20. The zinc oxide was included in the main (calcium carbonate-containing) dentifrice component only, and the zinc citrate was included in the stripe (silica abrasive-containing) dentifrice component only. Composition 2 also included 0.5 weight % TSPP (based on the total weight of the composition, i.e. the combined weight of the main dentifrice component and the stripe component). The TSPP was present in the stripe component only, with the main dentifrice component being free of TSPP.

Composition 3 was equivalent to Composition 2, with the difference that the 0.5 weight % TSPP (based on the total weight of the composition) was present in both the main dentifrice component and the stripe component, with 0.4 weight % TSPP (based on the total weight of the composition) being present in the main dentifrice component and 0.1 weight % TSPP (based on the total weight of the composition) being present in the stripe component.

Composition 4 was a calcium carbonate-based non-striped toothpaste, which also contained 0.5 weight % TSPP.

Composition 5 was a striped toothpaste with a calcium carbonate-based main dentifrice component and a silica abrasive-based stripe component. The weight ratio of the main dentifrice component to the stripe component was 80:20. The zinc citrate was included in the main (calcium carbonate-containing) dentifrice component only, and the zinc oxide was included in the stripe (silica abrasive-containing) dentifrice component only. Composition 5 also included 0.5 weight % TSPP (based on the total weight of the composition, i.e. the combined weight of the main dentifrice component and the stripe component). The TSPP was present in both the main dentifrice component and the stripe component, with 0.4 weight % TSPP (based on the total weight of the composition) being present in the main dentifrice component and 0.1 weight % TSPP (based on the total weight of the composition) being present in the stripe component.

Composition 6 was a striped toothpaste with a calcium carbonate-based main dentifrice component and a silica abrasive-based stripe component. The weight ratio of the main dentifrice component to the stripe component was 80:20. The zinc oxide was included in the main (calcium carbonate-containing) dentifrice component only, and the zinc citrate was included in the stripe (silica abrasive-containing) dentifrice component only. Composition 6 also included 1 weight % tetrasodium pyrophosphate (TSPP) and 1 weight % tetrapotassium pyrophosphate (TKPP) (both based on the total weight of the composition, i.e. the combined weight of the main dentifrice component and the stripe component). The TSPP and TKPP were present in both the main dentifrice component and the stripe component, with 0.8 weight % TSPP (based on the total weight of the composition) and 0.8 weight % TKPP (based on the total weight of the composition) being present in the main dentifrice component, and 0.2 weight % TSPP (based on the total weight of the composition) and 0.2 weight % TKPP (based on the total weight of the composition) being present in the stripe component.

Composition 7 was a striped toothpaste, in which both the main and the stripe components were silica abrasive-based. The weight ratio of the main dentifrice component to the stripe component was 80:20. Composition 7 contained 2 weight % zinc citrate, based on the total weight of the composition, and 2.44 weight % TKPP, based on the total weight of the composition. The zinc citrate was present in both the main dentifrice component and the stripe component, with 1.6 weight % zinc citrate (based on the total weight of the composition) being present in the main dentifrice component and 0.4 weight % zinc citrate (based on the total weight of the composition) being present in the stripe component. The TKPP was present in both the main dentifrice component and the stripe component, with 1.95 weight % TKPP (based on the total weight of the composition) being present in the main dentifrice component and 0.49 weight % TKPP (based on the total weight of the composition) being present in the stripe component.

Composition 8 was a silica abrasive-based non-striped toothpaste, which contained no zinc compounds. Composition 8 contained 0.5 weight % TSPP.

The Biofilm Growth Inhibition University of Manchester Model was used to determine the ability of Compositions 1 to 8 to reduce oral biofilms.

The protocol for this model is as follows:
(1) Dental plaque was collected from four healthy volunteers and pooled together as inoculum. The Optical Density of the inoculum was matched to 0.3 absorbance at 610 nm.
(2) Sterile hydroxyapatite (HAP) disks were incubated under anaerobic conditions at 37° C. for 24 hours with 1 mL of sterile artificial saliva (with 0.01 weight % sucrose) and 1 mL of pooled saliva in a 24 well microplate.
(3) For each composition, a treatment solution of 1 part dentifrice: 2 parts sterile distilled water by weight was made up. Each freshly prepared treatment solution was added to three wells and allowed to contact the HAP disk therein for 10 minutes.
(4) The liquid phase of each well was then removed and was replaced by 2 mL sterile artificial saliva.
(5) The disks were then maintained at 37° C. under anaerobic conditions for 8 days.
(6) At intervals of 2, 4 and 8 days, the disks were collected aseptically and transferred to half-strength pre-reduced thioglycollate medium (4.5 mL per disk).
(7) 100 µL of the dilution 10-4, 10-5 and 10-6 were plated in duplicates for each disk on Neomycin/Vancomycin (NV) Agar for Total Gram-negative Anaerobes.
(8) The plates were surface-spread using a sterile spreader and were incubated anaerobically at 37° C. for 72 hours, after which time the number of colonies on each plate was counted.
(9) The pH1 was monitored for the entire period of the study using the liquid phase.

The log 10 CFU/ml (where CFU=colony forming units) for each composition was calculated. A lower Log 10 CFU/ml indicates that the composition tested has greater efficacy in inhibiting biofilm growth. The results for Compositions 1 to 8 (showing the average of the log 10 CFU/ml over the three wells prepared for each composition) are shown in Table 1, below:

TABLE 1

Same superscript letter indicates avg log CFU not significantly different.

| Composition | Formula | Avg log CFU |
|---|---|---|
| 1 | Non-striped: 1 wt % ZnO/0.5 wt % ZnCit/0.5 wt % TSPP in a silica abrasive-based dentifrice. | $4.57^G$ |
| 2 | Striped: 1 wt % ZnO/0.5 wt % ZnCit/0.5 wt % TSPP. ZnO in CaCO$_3$-based component; ZnCit and TSPP in silica abrasive-based component. | $4.83^F$ |
| 3 | Striped: 1 wt % ZnO/0.5 wt % ZnCit/0.5 wt % TSPP. ZnO in CaCO$_3$-based component; ZnCit in silica abrasive-based component; TSPP distributed between both CaCO$_3$-based component and silica abrasive-based component. | $5.08^E$ |
| 4 | Non-striped: 1 wt % ZnO/0.5 wt % ZnCit/0.5 wt % TSPP in a CaCO$_3$-based dentifrice. | $5.11^E$ |
| 5 | Striped: 1 wt % ZnO/0.5 wt % ZnCit/0.5 wt % TSPP. ZnO in silica abrasive-based component; ZnCit in CaCO$_3$-based component; TSPP distributed between both CaCO$_3$-based component and silica abrasive-based component. | $5.34^D$ |
| 6 | Striped: 1 wt % ZnO/0.5 wt % ZnCit/1 wt % TSPP/1 wt % TKPP. ZnO in CaCO$_3$-based component; ZnCit in silica abrasive-based component; TSPP and TKPP distributed between both CaCO$_3$-based component and silica abrasive-based component. | $5.49^C$ |
| 7 | Striped silica abrasive-based dentifrice with 2 wt % ZnCit and 2.44 wt. % TKPP. | $5.80^B$ |
| 8 | Non-striped: 0.5 weight % TSPP in a silica abrasive-based dentifrice. No zinc compounds present | $6.89^A$ |

As can be seen from Table 1, above, the calcium carbonate-containing formulation which exhibited the highest biofilm reduction efficacy was Composition 2, which was a striped dentifrice containing 1 wt % ZnO, 0.5 wt % ZnCit and 0.5 wt % TSPP, wherein the zinc oxide was contained in the calcium carbonate-based component; and the zinc citrate and TSPP were contained in the silica abrasive-based component. As well as exhibiting higher biofilm reduction efficacy than all of the other striped compositions, this Composition also exhibited higher biofilm reduction efficacy than the non-striped calcium carbonate-based composition (Composition 4). Without being bound by any theory, it is thought that incorporation of the zinc citrate into the silica abrasive-based component, and incorporation of the zinc oxide into the calcium carbonate-based component, reduces the interaction of the soluble zinc salt with the calcium carbonate and hence improves the biofilm reduction efficacy of the composition.

The results above also show that the striped composition wherein the zinc oxide was contained in the silica abrasive-based component and the zinc citrate was contained in the calcium carbonate-based component (Composition 5) exhibited lower biofilm reduction efficacy than the non-striped composition with both zinc citrate and zinc oxide incorporated in a calcium-carbonate base (Composition 4).

The results above also indicate that, for the striped compositions tested, the biofilm reduction efficacy was further affected by the location of the TSPP in the oral care composition i.e. whether it was present in the silica abrasive-based component alone, or whether it was present in both the silica abrasive-based component and in the calcium carbonate-based component. Surprisingly, the above results show that the biofilm reduction efficacy was higher for a composition comprising 0.5 wt. % TSPP in the silica abrasive-based component alone (Composition 5) than for an equivalent composition which differs only in that the 0.5 wt. % TSPP is present in both the silica abrasive-based component and in the calcium carbonate-based component (Composition 3).

The results above also indicate that, for the compositions tested, the composition containing a higher concentration of the pyrophosphate tartar control agents (Composition 6, which contained 1 wt. % TSPP and 1 wt. % TKPP) exhibited lower biofilm reduction efficacy than the compositions which contained a lower concentration of the pyrophosphate tartar control agent (Compositions 1 to 5, each of which contained 0.5 wt. % TSPP). In particular, the biofilm reduction efficacy of Composition 6 (1 wt. % TSPP and 1 wt. % TKPP) was lower than for an equivalent composition which differed only in that it contained a lower concentration of tartar control agent (Composition 3, which contained 0.5 wt. % TSPP). Without being bound by any theory, it is thought that, when higher levels of pyrophosphate are present, the pyrophosphate may chelate zinc ions and decrease their efficacy.

What is claimed is:

1. An oral care composition comprising:
  (a) a first composition comprising a silica abrasive and a first zinc compound selected from zinc citrate, zinc chloride, zinc acetate, zinc lactate, zinc salicylate, zinc sulfate, and zinc nitrate; and
  (b) a second composition comprising a calcium carbonate abrasive; wherein the second composition further comprises a second zinc compound and wherein the second zinc compound is zinc oxide.

2. The oral care composition of claim 1, wherein the oral care composition further comprises from 0.1 to 1.75 weight % of a tartar control agent, based on the total weight of the oral care composition.

3. The oral care composition of claim 1, wherein the concentration of the first zinc compound in the oral care composition is from 0.25 to 0.75 weight % based on the total weight of the oral care composition.

4. The oral care composition of claim 1, wherein the concentration of the second zinc compound in the oral care composition is from 0.5 to 1.5 weight %, based on the total weight of the oral care composition.

5. The oral care composition of claim 1, wherein the weight ratio of the second zinc compound to the first zinc compound in the oral care composition is from 1.5:1 to 4.5:1.

6. The oral care composition of claim 1, wherein the first zinc compound is zinc citrate.

7. The oral care composition of claim 1, wherein the concentration of the silica abrasive in the oral care composition is from 1 to 10 weight %, based on the total weight of the composition.

8. The oral care composition of claim 1, wherein the concentration of the calcium carbonate abrasive in the oral care composition is from 20 to 40 weight %, based on the total weight of the composition.

9. The oral care composition of claim 1 wherein the first composition is a toothpaste.

10. The oral care composition of claim 1 wherein the first composition is a gel.

11. The oral care composition of claim 1 wherein the second composition is a toothpaste.

12. The oral care composition of claim 1, wherein the weight ratio of the first composition to the second composition is from 1:8 to 1:1.

13. The oral care composition of claim 1, wherein the oral care composition is a striped dentifrice comprising a main dentifrice material and a stripe dentifrice material, the first composition being the stripe dentifrice material and the second composition being the main dentifrice material.

14. The oral care composition of claim 2, wherein the tartar control agent is a monobasic, dibasic or tribasic sodium phosphate; a mono-, di- or trisodium pyrophosphate; a mono-, di- or tripotassium pyrophosphate; tetrasodium pyrophosphate (TSPP); tetrapotassitim pyrophosphate (TKPP); sodium or potassium tripolyphosphate; sodium or potassium tetrapoiyphosphate; sodium or potassium trimetaphosphate; sodium or potassium hexametaphosphate; or a combination of any two or more thereof.

15. The oral care composition according to claim 1, wherein the composition comprises a fluoride source.

16. The oral care composition according to claim 15, wherein the fluoride source is at least one selected from stannous fluoride, sodium fluoride, potassium fluoride, sodium monofluorophosphate, sodium fluorosilicate, ammonium fluorosilicate, amine fluoride, and ammonium fluoride.

17. A method of reducing or inhibiting biofilm formation in an oral cavity, the method comprising contacting the oral cavity with an oral care composition according to claim 1.

18. A method of enhancing the antibacterial efficacy of an oral care composition comprising a calcium carbonate abrasive and at least one zinc salt, the method comprising providing the oral care composition according to claim 1 as an oral care composition.

19. A method of forming an oral care composition, comprising adding
  (a) a first composition comprising a silica abrasive and a first zinc compound selected from zinc citrate, zinc chloride, zinc acetate, zinc lactate, zinc salicylate, zinc sulfate, and zinc nitrate; to
  (b) a second composition comprising a calcium carbonate abrasive;

wherein the second composition further comprises a second zinc compound and wherein the second zinc compound is zinc oxide;
and wherein the concentration of the first zinc compound in the second composition is less than 0.01 weight %, based on the weight of the second composition.

\* \* \* \* \*